United States Patent [19]

Wright et al.

[11] Patent Number: 5,595,759
[45] Date of Patent: Jan. 21, 1997

[54] PROCESS FOR PROVIDING THERAPEUTIC COMPOSITION

[75] Inventors: Jeri D. Wright, Dublin; Brian L. Barclay, Sunnyvale; Linda E. Atkinson, Portola Valley, all of Calif.

[73] Assignee: Alza Corporation, Palo Alto, Calif.

[21] Appl. No.: 337,701

[22] Filed: Nov. 10, 1994

[51] Int. Cl.⁶ .................................................. A61K 9/20
[52] U.S. Cl. ........................ 424/464; 424/465; 424/474; 424/480
[58] Field of Search .......................... 424/464, 465, 424/473, 474, 479, 484, 486, 426

[56] References Cited

U.S. PATENT DOCUMENTS

| | | | |
|---|---|---|---|
| 2,799,241 | 7/1957 | Wurster | 118/24 |
| 3,133,132 | 5/1964 | Loeb et al. | 264/49 |
| 3,845,770 | 11/1974 | Theeuwes et al. | 128/130 |
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/260 |
| 4,160,020 | 7/1979 | Ayer et al. | 424/15 |
| 4,177,256 | 12/1979 | Michaels et al. | 424/22 |
| 4,200,098 | 4/1980 | Ayer et al. | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,449,983 | 5/1983 | Cortese et al. | 604/892 |
| 4,772,474 | 9/1988 | Eckenhoff et al. | 424/465 |
| 4,814,182 | 3/1989 | Graham et al. | 424/484 |
| 4,948,593 | 8/1990 | Wright et al. | 424/473 |
| 5,032,406 | 7/1991 | Dansereau et al. | 424/472 |
| 5,098,714 | 3/1992 | Wright et al. | 424/473 |
| 5,200,197 | 4/1993 | Wright et al. | 424/473 |

OTHER PUBLICATIONS

Wurster, Dale E. J. Am. Pharm. Assn., Sci. Ed., vo. 49, (1960) pp. 82–84.
Wurster, Dale E., J. Am. Pharm. Assn., Sci. Ed., vol. 48 (1959) pp. 451–454.
The Pharmacological Basis of Therapeutics, by Goodman & Gilman, 7th Ed., (1985) pp. 1430–1439.
Pharmaceutical Sciences, by Remington, 14th Ed., (1970) pp. 1626–1680.

*Primary Examiner*—Thurman K. Page
*Assistant Examiner*—Sharon Howard
*Attorney, Agent, or Firm*—Paul L. Sabatine; Mary Ann Dillahunty; Felissa H. Cagan

[57] ABSTRACT

A process is disclosed and claimed for preparing a therapeutic composition comprising asteroid or a dosage form comprising the composition, which therapeutic composition or dosage form is indicated for human administration.

7 Claims, No Drawings

PROCESS FOR PROVIDING THERAPEUTIC COMPOSITION

FIELD OF THE INVENTION

This invention pertains to a therapeutic composition, to a dosage form, and to a process for preparing the therapeutic composition, and the dosage form. The therapeutic composition and the dosage form comprise a drug, for example, a pharmaceutically acceptable steroid selected from an estrogen, or a progestin, or both an estrogen and a progestin.

BACKGROUND OF THE INVENTION

The direction of much medical and scientific research in recent prior art endeavors has been to provide a therapeutic composition comprising a drug, or to provide a dosage form comprising a drug indicated in both instances for therapy, or for contraception. In the latter, the therapeutic composition, and the dosage form are a means for administering a therapeutically acceptable progestin to a human. The prior art, in recent patents, U.S. Pat. Nos. 4,948,593; 5,098,714; and 5,200,197 all issued to Wright et al, there are disclosed compositions comprising an estrogen and a progestin that are administered for contraceptive purposes. While these compositions operate successfully for their intended purpose, it has now been discovered a process can be provided that improves the manufacture of the composition and correspondingly a dosage form containing the composition. The present invention has an object to provide a process for preparing a therapeutic composition comprising a member selected from the group consisting of an estrogen, a progestin, or a combination of an estrogen and a progestin, which can be administered as a composition, or administered from a dosage form. The invention further has an object to provide a method for administering a composition for contraception which composition is produced by the process of the invention.

DESCRIPTION FOR PROVIDING THE INVENTION

In providing the process to produce the composition, and the dosage form, the estrogen contraceptively acceptable for these purposes comprise a member selected from the group consisting of estrogen, estradiol, estradiol valerate, estradiol benzoate, estradiol cypionate, estradiol ether, estradiol ester, estradiol propionate, estradiol dipropionate, estradiol acetate, ethinyl estradiol esters, 17α-ethinyl estradiol acetate, 17α-ethinyl estradiol benzoate, 17α-ethinyl estradiol ethers, 17α-ethinyl estradiol ethers, estrone, estrone acetate, estrone sulfate, estriol, estriol succinate, 17β-estradiol, ethinyl estradiol 17-methyl ether, ethinyl estradiol 3-anthranilate hydrochloride, ethinyl estradiol 3-methyl ether, ethinyl estradiol 3, 17-dimethyl ether, ethinyl estradiol-17-ethyl ether, and estrone phosphate. The dosage amount of estrogen or estrogen derivative in a composition is 1 ng to 1000 mg.

In providing the process for producing the therapeutic composition and the dosage form, the progestin for these purposes comprise a member selected from the group consisting of progesterone, d-norgestrel, norethindrone, levonorgestrel, norgestimate, norethisterone, norethisterone acetate, norethynodrel, norethindrone acetate, 17-hydroxyprogesterone, 17-hydroxyprotesterone ester, 17-hydroxyprogesterone ether, 19-nor-17-hydroxyprogesterone, 19-nor-17-hydroxyprogesterone ester, 19-nor-17-hydroxyprogesterone ether, 17β-acetoxy-13β-ethyl-17α-ethinyl-gon-4-en-3-one oxime, d-13β-ethyl-17α-ethinyl-17β-hyroxygon-4-en-3-one, 13β-ethyl-17β-hydroxygon-4-en-3-one, 13β,17β-diethyl-17β-hydroxygon-4-en-3-one, ethylnodiol diacetate, medroxyprogesterone, chlormadione acetate, 17α-ethinyl-17β-acetoxy-17-norandrost-4-en-3-one, 3-ketodesogestrel, desogestrel, gestodene, gestodene acetate, levonorgestrel-2-methylbutanoate, levonorgestrel acetate, levonorgestrel butanoate, levonorgestrel butyrate, levonorgestrel cyanoacetate, levonorgestrel cyclobutane carboxylate, levonorgestrel cyclopropylcarboxylate, norgestrel decanoate, norgestrel pentanoate, norgestrel-2-methyl-2-enoate, norgestrel formate, norgestrel glycidol, norgestrel keptanoate, norgestrel hexanoate, northisterone methoxyacetate, northisterone nonanoate, northisterone pentanoate, desogestrel propanoate, desogestrel valerate, desogestrel-2-ethylbutanoate, desogestrel cyclobutylheptanoate, and d, l-norgestrel. The dosage of progestin or progestin derivatives in a composition is 10 ng to 500 mg.

In providing the process for producing the composition, and the dosage form containing the composition the process provides also a combination of an estrogen and a progestin selected from the combination consisting of ethinyl estradiol and cyproterone acetate, ethinyl estradiol and desogestrel, ethinyl estradiol and dimethisterone, ethinyl estradiol and ethylnodiol diacetate, ethinyl estradiol and ethynodiol diacetate, ethinyl estradiol and gestodene, ethinyl estradiol and gestodene, ethinyl estradiol and levonorgestrel, ethinyl estradiol and lynestrenol, ethinyl estradiol and norethindrone acetate, ethinyl estradiol and norethindrone propionate, ethinyl estradiol and norethindrone, ethinyl estradiol and norethindrone butyrate, ethinyl estradiol and norethindrone palmitate, ethinyl estradiol and norethisterone, ethinyl estradiol and norgestrel, ethinyl estradiol and norgestimate, ethinyl estradiol and norethynodrel, ethinyl estradiol and progesterone, ethinyl estradiol and hydroxyprogesterone, estrone and progesterone, estrogen and progesterone, estrogen and levonorgestrel, estrogen and norgestrel, estrogen and norethindrone, estrogen and norgestimate, estrogen and norethisterone, estrogen and norethynodrel, estrogen and hydroxyprogesterone, estrogen and desogestrel, estrogen and gestodene, estriol and desogestrel, estriol and gestodene, estriol and desogestrel, estriol and gestodene, estriol and levonorgestrel, estriol and norethindrone, estriol and norgestrel, estriol and norgestimate, estriol and progesterone, estriol and hydroxyprogesterone, estriol and desogestrel, estriol and dimethisterone, and estriol and norethisterone. The composition consisting of a contraceptive pair of an estrogen and progestin comprises 11 ng to 1750 mg of the steroid pair.

A process for providing a composition consisting of levonorgestrel (LNG) and ethinyl estradiol (EE) comprises the following process steps: 3.835 g of micronized ethinyl estradiol is dissolved in an organic solvent, ethyl alcohol, 1777.5 g with constant stirring to produce a wet granulation. Next, separately, 18.335 g of levonorgestrel is mixed in a blender with 250 g of a hydroxyalkylcellulose, hydroxypropylmethylcellulose possessing a 11,200 molecular weight to yield a drug levonorgestrelhydroxypropylmethyl-cellulose homogenous blend. Then, an osmopolymer, poly(alkylene oxide), 4702.83 g of poly(ethylene oxide) possessing a 200,000 molecular weight, is added to the blend comprising the levonorgestrel and the hydroxypropyl-methylcellulose and the three ingredients, the poly(ethylene oxide), hydroxypropylmethylcellulose and the levonorgestrel blended into a homogenous blend for 10 minutes. Next, the ethinyl estradiol granulation is added slowly to the dry three-ingredient blend and the blending continued for 7 to 9 minutes. Next, the just prepared wet blend comprising the four ingredients is screened through a 20 mesh screen and the wet granules dried overnight at room temperature to evaporate the solvent. Then, optionally, a lubricant, magnesium stearate, 25 g is added to the dried granules to yield the contraceptive composition. The composition can be compressed into tablets comprising 0,023 mg of ethinyl estradiol, 0.110 mg of levonorgestrel, 28.217 mg of poly(ethylene oxide), 1.50 mg of hydroxypropylmethylcellulose, and 0.150 mg of magnesium stearate. In another process, the composition can comprise 4.65 mg of lactose. In the above process, a different embodiment comprises blending the hydroxyalkylcellulose and the epoxy(alkylene oxide) as the initial or first step followed by the other processing steps.

The composition prepared by the process can be manufactured into a dosage form. The dosage form provides controlled-release sustained-release physico-chemical properties by encapsulating the composition with a polymer, such as cellulose acetate. The composition can also be manufactured into a dosage form comprising a layer of the composition, and a push layer comprising an osmopolymer of 2,500,000 to 7,800,000 molecular weight which composition and push layer are encapsulated by a polymer, cellulose acetate possessing 39.8% acetyl content formed from a solvent, 95% acetone-5% water. The dosage form is freed of solvent by drying the dosage form for 120 hours at 50° C. and 50% relative humidity. The dosage form comprises an exit means of releasing the composition over 8 to 24 hours. The dosage form delivers 20 mcg of ethinyl estradiol and 100 mcg of levonorgestrel at a T90 of 20 hours.

The procedures presented above are followed to prepare the following compositions: (1) a composition comprising 0.0767% ethinyl estradiol, 0.3667% levonorgestrel, 94.0566% poly(ethylene oxide) possessing a 200,000 molecular weight, 5.00% hydroxypropylmethylcellulose of 11,200 molecular weight and 0.500% magnesium stearate, with the total weight of the composition 30 mg; and (2) a composition comprising 0.0767% ethinyl estradiol, 0.3667% levonorgestrel, 94.0566% sodium carboxymethylcellulose having a 90,000 molecular weight, 5.000% hydroxypropylcellulose of 95,000 molecular weight and 0.5000% magnesium stearate. The composition comprising the steroid pair weighed 30 mg.

The procedures presented above followed for preparing the following compositions: (1) a push composition comprising 63.675% poly(ethylene oxide) of 7,500,000 molecular weight, 30.000% sodium chloride, 5.000% hydroxypropylmethylcellulose of 11,200 molecular weight, 1.00% iron oxide, 0.250% magnesium stearate, and 0.075% butylhydroxytoluene, with the composition weighing 30 mg; and (2) a push, osmotic composition comprising 78.8% sodium carboxymethylcellulose of 90,000 to 1,000,000 molecular weight, 10% sodium chloride, 5.5% poly(vinylpyrrolidone) of 40,000 molecular weight, 4.5% poly(vinylpyrrolidone) of 90,000 molecular weight, 1.0% iron oxide, and 0.2% magnesium stearate, with the total weight of the push composition equal to 30 mg.

Dosage forms, comprising the above steroid composition and push compositions are prepared as follows: a two-layered press is used for forming a bilayered arrangement; first 30 mg of the composition comprising 0.0767% ethinyl estradiol, 0.3667% of levonorgestrel, 94.0566% of poly(ethylene oxide) of 200,000 molecular weight, 5.00% of hydroxypropylmethylcellulose of 11,200 molecular weight and 5.000% of magnesium stearate is added to the press and tamped; then 30 mg of the push composition comprising 63.675% poly(alkylene oxide) of 7,800,000 molecular weight, 30,000% sodium chloride, 5.00% hydroxypropylmethylcelllulose, 1.00% iron oxide, 0.250% magnesium stearate and 0.075% butylene hydroxytoluene, is added to the press as a second layer and the two layers pressed into a contacting layered arrange-ment. Next, the two layers are surrounded with a semipermeable wall comprising 100% cellulose acetate possessing an acetyl content of 39.8%. The wall forming composition is sprayed from an acetone-water, 95:5 wt:wt, solvent using an Vector LDCS® Coater. An 0.600 mm passageway is drilled on the contraceptive layer of the osmotic dosage form. Finally, any residual solvent is removed by drying for 120 hours at 50° C. and 50% relative humidity.

The dosage form comprising the contraceptive layer and the push-expandable layer disclosed immediately above is made in this embodiment with the condition as previously disclosed except in this embodiment the semipermeable wall permeable to aqueous fluids and impermeable to steroids comprises 80% cellulose acetate consisting of 39.8% acetyl content, and 20% poly(vinyl acetate) of 37,500 molecular weight. In another embodiment, the wall composition comprises 68% cellulose acetate having an acetyl content of 39.8%, 30% Eudragit RS100, a polymer synthesized from acrylic and methacylic acid esters and 2% polyethylene glycol of 3350 molecular weight.

The invention provides another dosage form comprising asteroid composition and a push composition, as follows: first, 30 mg of asteroid composition comprising 0.0767% ethinyl estradiol, 0.3667% levonorgestrel, 94.0566% poly(ethylene oxide) of 100,000 to 300,000 molecular weight, 5.00% hydroxypropylmethylcellulose of 11,200 molecular weight, and 0.50% of magnesium stearate is added to a press and tamped into asteroid layer; then, 30 mg of a push composition comprising 78.8% sodium carboxymethylcellulose of 700,000 molecular weight, 10.00% sodium chloride, 5.5% poly(vinylpyrrolidone) 40,000 molecular weight, 4.5% poly(vinylpyrrolidone) of 90,000 molecular weight, 1.0% ferric oxide, and 0.2% magnesium stearate is added to the press and compressed in a push layer to form a bilayer core. Next, the bilayer core is surrounded with a semipermeable wall selected from the group of wall compositions as follows: (1) a wall composition comprising 100% cellulose acetate possessing an acetyl content of 39.8%; (2) a wall forming composition comprising 80% cellulose acetate possessing an acetyl content of 39.8% and 20.0% poly(vinyl acetate) of 90,000 molecular weight; or (3) a wall composition comprising 68.0% cellulose acetate possessing a 39.8% acetyl content, 30.0% Eudragit RS100 a polymer synthesized from acrylic and methacrylic acid ester, and 2.0% poly(ethylene glycol) possess a 3350 molecular weight. The wall are formed by a suspension coating and the final dosage form possess an exit of 0.45 mm and release the steroid pair at a controlled rate up to 24 hours.

A dosage form comprising asteroid layer and a push layer is provided by following the above procedures. The steroid layer comprises 0.0767% ethinyl estradiol, 0.3667% levonorgestrel, 94.0566% sodium carboxymethyl-cellulose, 5.00% hydroxypropylcellulose and 0.500% magnesium stearate; the push layer comprises 78.8% sodium carboxymethylcellulsoe, 10.0% sodium chloride, 5.5% poly(vinylpyrrolidone) of 40,000 molecular weight, 4.5% poly(vinylpyrrolidone) of 90,000 molecular weight, 1.0% ferric oxide, and 0.2% potassium stearate; and, a push layer comprising 83.75% sodium carboxymethylcellulose 7H4F of 700,000 molecular weight, 10.00% sodium chloride, 5.00% hydroxypropylcellulose, 1.00% iron oxide and 0.25% magnesium stearate; a wall comprising 68.0% cellulose acetate containing 39.8% acetyl content, 30.0% Eudragit RS100 a polymer synthesized from arcylic and methacylate acid ester, and 2.0% polyethylene glycol of 3350 molecular weight; and a pair of exits of 0.25 mm through the semipermeable wall connecting the steroid composition with the exterior of the dosage form.

In the process of this invention, the term polymer used to provide a semipermeable composition that surrounds or encapsulates a therapeutic composition or is used for providing a controlled-sustained release dosage form comprises a cellulose polymer selected from the group consisting of a cellulose ester, cellulose ether, cellulose ester-ether, cellulose acylate, cellulose diacylate, cellulose triacylate, cellulose acetate, cellulose diacetate and cellulose triacetate. The cellulose polymers comprise a degree of substitutions, D.S., on the anydroglucose unit from greater than 0 up to 3, inclusive. By degree of substitution is meant the average number of hydroxyl groups originally present on the anydroglucose unit comprising the cellulose polymer that are replaced by a substituting group.

Exemplary polymers comprise cellulose acetate having a D.S. up to 1 and an acetyl content up to 21%; cellulose acetate having an acetyl content of 32% to 39.8%; cellulose diacetate having a D.S. of 1 to 2 and an acetyl content of 21% to 35%; cellulose triacetate having a D.S. of 2 to 3 and an acetyl content of 35% to 44.8%, and the like. Other examples comprise cellulose propionate having a D.S. of 1.8, a propanol content of 39.2% to 45% and a hydroxy content of 2.8% to 5.4%; cellulose acetate butyrate having a D.S. of 1.8, and acetyl content of 13% to 15% and a butyryl content of 34% to 39%; cellulose acetate butyrate having an acetyl content of 2% to 29%, a butyryl content of 17% to 53% and a hydroxy content of 0.5% to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentale, and the like. Additional cellulose polymers that may be present in a wall comprise ethyl cellulose comprising an ethoxy group degree of substitution of 1.5 to 3, about 40% to 50% ethoxy content, and a viscosity range of 7 to 100 centipoises, or higher; a cellulose ether selected from the group consisting of hydroxypropylcellulose, hydroxybutylcellulose, hydroxypropylmethylcellulose and hydroxyethylcellulose, and the like. In one preferred manufacture a wall comprises 100 weight percent (wt %) of a cellulosic polymer as disclosed above; in another preferred manufacture the wall comprises from 60 weight percent to 90 weight percent of a member selected the group consisting of a cellulose acylate, cellulose diacylate and cellulose triacylate polymer, from 15 to 45 weight percent of an ethyl cellulose and from 0 to 25 weight percent of a polyethylene glycol with the total amount of all wall-components comprising the wall equal to 100 weight percent; and another embodiment comprising 45 to 80 weight percent of a member selected from the group consisting of a cellulose acylate, cellulose diacylate and cellulose triacylate, from 15 to 45 weight percent of an ethyl cellulose triacylate, from 15 to 45 weight percent of an ethyl cellulose, from 0.5 to 25 weight percent of a cellulose ether selected from the group consisting of hydroxypropylcellulose, hydroxybutylcellulose, hydroyethylcellulose, and hydroxypropylmethylcellulose, and from 0 weight percent to 30 weight percent of polyethylene glycol, with the total amount of all components comprising the wall equal to 100 weight percent. The cellulosic polymers are known in US Pat. Nos. 3,133,132; 3,845,770; 3,916,899 and 4,160,020; and in the *Handbook of Common Polymers* by Scott, J. R. and Roff, W. J. (1971) published by CRC Press, Cleveland, Ohio.

The expression, "exit means", as used herein, comprises means and methods suitable for the controlled metered release of steroid from a dosage form. The exit means is sized and adapted for the metered release of steroid from the dosage form. The exist means includes at least one passageway, orifice, or the like, through the wall for communicating with the contraceptive steroids dosage in the dosage form. The expression, "at least one passageway", incudes aperture, orifice, bore, pore, porous element, and the like, through which the contraceptive steroids can migrate, a hollow fiber, capillary tube, porous overlay, porous insert, composite semipermeable contacting microporous insert, or the like. The expression incudes also a material that erodes or is a material that is leached from the wall in a fluid environment of use to produce at least one passageway in the wall. Representative materials suitable for forming at least one passageway, or a multiplicity of passageways, include an erodible polyglycolic acid, or a polylactic acid member in the wall, a gelatinous filament, polyvinyl, alcohol, a leachable material such as a fluid removable pore forming polysaccharide, polyol, salts, oxide, or the like. A passageway, or a plurality of passageways can be formed by leaching a material such as sorbitol, fructose, realrose, lactose, or the like, from the wall. The passageway can have any shape such as round, triangular, square, elliptical, and the like, for assisting in the metered release of the contraceptive steroids from the dosage form. The dosage form can be constructed with one or more passageway in spaced apart relation, or more than one passageway on a single surface of the dosage form. Passageways and equipment for forming passageways are disclosed in U.S. Pat. Nos. 3,845,770 issued to Theeuwes et al; 4,063,064 issued to Saunders et al; and in U.S. Pat. No. 4,088,864 issued to Theeuwes et al. Passageways in osmotic systems formed by leaching are disclosed in U.S. Pat. Nos. 4,200,098 issued to Ayer et al; in U.S. Pat. Nos. 4,285,987 issued to Ayer et al; in U.S. Pat. No. 4,309,996 issued to Theeuwes; and in U.S. Pat. No. 4,320,759 issued to Theeuwes.

Exemplary solvents for the purpose of this invention include inert inorganic and organic solvents that do not adversely harm the composition, the dosage form, the materials, and the final wall. The solvents broadly include a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptone, ethylene glycol monoethyl ether, ethylene glycol monoethyl ether, ethylene glycol monoethyl acetate, methylene dichloride, ethylene dichloride, propylene dichloride, water, acetone and water, acetone and methanol, acetone and ethyl alcohol, methylene dichloride and methanol, ethylene dichloride and methanol.

The hydroxyalkylcellulose used in the process comprises a member selected from the group consisting of hydroxyalkylcellulose, hydroxypropyl-cellulose, hydroxyethylcellulose, hydroxybutylcellulose, hydroxypropylmethyl-cellulose, hydroxypropylethylcellulose, hydroxypropylesopropylcellulose, hydroxypropylbutylcellulose, hydroxypropylpentylcellulose, and hydroxy-propylhexylcellulose. The hydroxyalkylcellullose comprises a 7,500 to 175,000 molecular weight.

The term osmagent, as used herein, also includes osmotically effective solute, osmotically effective compounds, and osmotic agent. The osmotically effective compounds that can be used for the purpose of this invention include inorganic and organic compounds that exhibit an osmotic pressure gradient across a wall against an external fluid. Osmotically effective compounds useful for the present process include magnesium sulfate, magnesium chloride, sodium chloride, lithium chloride, potassium sulfate, sodium carbonate, sodium sulfite, lithium sulfate potassium chloride, calcium bicarbonate, sodium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixture thereof. The compound can be in any physical form such as particle, crystal, pellet, ground, pulverized, or granule.

The osmopolymer acceptable for the process of blend with the estrogen, or the progestin comprise hydrophilic polymers that are noncrosslinked, or crosslinked with ionic, hydrogen or covalent bonds. The osmopolymer blended with the estrogen or progestin interact with water or aqueous-biological fluids and form a dispensable solution, suspension or dispensable viscous composition that can be delivered to a human. The osmopolymer can be of plant, animal or of synthetic origin. Representative osmopolymers comprise hydrophilic polymers comprising a 10,000 to 650,000 molecular weight comprising poly(hydroxyalkyl methacrylate), poly(vinyl alcohol), agar, agarose, alginates, amylopectin, arabinoglactan, carrageen, eucheuma, fucolian, furcellaran, gelatin, guar gum, gum agar gum arabic, gum ghatti, gum karaya, gum tragacanth, hypnea, laminarin, locust bean gum, pectin, propylene glycol alginate, polysaccharide and xanthan gum. The polymers are known in *Controlled Release System, Fabrication Technology*, Vol. II (1988), published by CRC Press, Inc. Additional osmopolymer for blending in the process with the estrogen or the progestin comprise a 100,000 to 650,000 molecular weight as a member selected from the group consisting of poly(alkylene oxide), poly(methylene oxide), poly(ethylene oxide), poly(propylene oxide), poly(isopropylene oxide), poly(butylene oxide), poly(pentylene oxide), and poly(hexylene oxide). The poly(alkylene oxide) are available from the Union Carbide Corporation, Danbury, Colo.

The hydrogel, also identified as expandable polymer, and osmopolymer for forming an expandable or push composition for delivering the therapeutic composition from the dosage form at a controlled-sustained rate over time, comprise an osmopolymer having a 500,000 to 7,800,000 molecular weight, that imbibes fluid and thereby increased in volume for expanding against the therapeutic composition to push and deliver said composition through the exit means from a dosage form. The osmopolymer is represented by a poly(alkylene oxide) of the structure $(-O-CH_2CH_2)n$ wherein $n=45 \times 10^3$ to $17 \times 10^4$, said alkylene comprising a member selected from the group consisting of methylene, ethylene, propylene, isopropylene, butylene, pentylene and hexylene; the osmopolymer is further represented by a carboxyvinyl polymer of 700,000 to 4,500,000, and a carboxymethylcellulose of 500,000 to 5,250,000 molecular weight.

The lubricant for the present purpose comprise a member selected from the group consisting of magnesium stearate, calcium stearate, potassium stearate, lithium stearate, stearic acid, hydrogenated vegetable oil, magnesium oleate, stearyl alcohol, magnesium palmirate, and potassium arachidicate. The amount of lubricant in a composition is 0.02 mg to 3 mg.

The total percent of all ingredients in a composition is equal to 100%.

DISCLOSURE OF A METHOD OF USING THE INVENTION

An embodiment of the invention pertains to a method for delivering the contraceptive steroids in the dosage form comprising the composition prepared according to the manner of the invention. The method comprises administering at a rate controlled dose to a female desiring contraception by (1) admitting into the female orally a dosage form comprising a wall that surrounds a compartment, which wall comprises a semipermeable polymer composition permeable to fluid and impermeable to the passage of a contraceptive steroid; (2) a composition comprising an estrogen, or a composition comprising an estrogen and a progestin, in an amount for performing a contraceptive program; (3) a composition in the compartment comprising a hydrogel for imbibing and absorbing fluid causing the hydrogel to expand and push the composition comprising the estrogen, or the estrogen and the progestin from the dosage form; (4) at least one passageway in the wall for connecting the exterior of the dosage form with the interior of the dosage form; (5) delivering the contraceptive steroid from the dosage form through the exit passageway to the female for providing the desired contraception. The method provides by way of further example administering 1 micrograms to 10.0 milligrams of an estrogen, and 18 micrograms to 500 milligrams of a progestin, and the method provides also for administering the steroid for 21 to 28 days per month to provide contraception.

Inasmuch as the foregoing specification comprises preferred embodiments of the invention, it is understood that variations and modifications may be made herein, in accordance with the inventive principles disclosed, without departing from the scope of the invention.

What is claimed is:

1. A process for preparing a therapeutic composition for administering to a human, wherein the process comprises the steps of:

a) blending an estrogen with ethanol to produce a wet granulation;

b) blending separately a hydroxyalkylcellulose of 7,500 to 175,000 molecular weight with a poly(alkylene oxide) of 100,000 to 650,000 molecular weight to produce a dry granulation;

c) mixing the wet granulation and the dry granulation to produce a homogenous wet mixture;

d) evaporating the solvent from the mixture to produce dry granules; and, e) compressing the dry mixture into a shape and size adopted for oral administration to the human for delivering the therapeutic composition to the human.

2. The process for preparing the therapeutic composition of administering to a human according to claim 1, wherein the therapeutic composition comprises a progestin.

3. The process for preparing the therapeutic composition for administering to a human according to claim 1, wherein the process consists essentially of preparing step (b) prior to preparing step (a).

4. A process for preparing a dosage form, wherein the process comprises:

a) blending an estrogen with ethanol to provide a wet granulation;

b) blending an osmopolymer with the wet granulation to provide a homogenous wet blend;

c) evaporating the solvent from the blend to produce dry granules;

d) pressing the dry granules into a shaped composition;

e) coating the shaped composition with a semipermeable composition; and f) forming an exit in the semipermeable coating to provide the dosage form.

5. The process for preparing the dosage form according to claim 4, wherein the estrogenic steroid is blended with a progestin.

6. A process for preparing a dosage form, wherein the process comprises the step of:

a) blending an osmopolymer and a hydroxyalkylcellulose polymer to produce a dry blend;

b) blending estrogen with ethanol to form a wet granulation;

c) blending the wet granulation and the dry blend to provide a homogenous wet blend;

d) evaporating the solvent from the homogenous wet blend;

e) pressing the homogenous blend into a tablet-shaped composition;

f) coating the tablet-shaped composition with a semipermeable composition; and g) forming an exit means in the coating for delivering the estrogenic steroid from the dosage form.

7. The process for preparing the dosage form according to claim 6, wherein the estrogen is blended with a progestin.

* * * * *

UNITED STATES PATENT AND TRADEMARK OFFICE
CERTIFICATE OF CORRECTION

PATENT NO. : 5,595,759
DATED : January 21, 1997
INVENTOR(S) : Jeri D. Wright; Brian L. Barclay; Linda E. Atkinson It is certified that error appears in the above-indentified patent and that said Letters Patent is hereby corrected as shown below:

On the Title page: in line 2 of the Abstract, "asteroid" should be changed to read --a steroid--.

Signed and Sealed this

Twenty-seventh Day of May, 1997

Attest:

BRUCE LEHMAN

Attesting Officer     Commissioner of Patents and Trademarks